(12) United States Patent
Jarrard et al.

(10) Patent No.: US 10,598,664 B2
(45) Date of Patent: Mar. 24, 2020

(54) EPITHELIAL QUANTITATION OF HISTOLOGICALLY NORMAL PROSTATE TISSUE PREDICTS THE PRESENCE OF CANCER IN TISSUE BIOPSIES

(71) Applicant: Wisconsin Alumni Research Foundation, Madison, WI (US)

(72) Inventors: David Frazier Jarrard, Madison, WI (US); Bing Yang, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 15/812,015

(22) Filed: Nov. 14, 2017

(65) Prior Publication Data

US 2018/0136215 A1    May 17, 2018

Related U.S. Application Data (60) Provisional application No. 62/421,554, filed on Nov. 14, 2016.

(51) Int. Cl.
*G01N 33/574* (2006.01)
*G06K 9/00* (2006.01)
*G06T 7/00* (2017.01)

(52) U.S. Cl.
CPC ... *G01N 33/57434* (2013.01); *G06K 9/00147* (2013.01); *G06T 7/0012* (2013.01); *G01N 2800/7028* (2013.01); *G06K 2209/05* (2013.01); *G06T 2207/30024* (2013.01); *G06T 2207/30081* (2013.01)

(58) Field of Classification Search
None
See application file for complete search history.

(56) References Cited

U.S. PATENT DOCUMENTS

| 2012/0135877 A1 | 5/2012 | Jarrard |
| 2014/0296355 A1 | 10/2014 | Jarrard |

FOREIGN PATENT DOCUMENTS

| WO | 2007044944 | 4/2007 |

OTHER PUBLICATIONS

Chen et al. in Clinical Proteomics 10:18, 1-10 (2013) (Year: 2013).*
Aperio AT Turbo Brochure (retrieved from the intenet May 8, 2019) (Year: 2019).*
Shipitsin et al. In Proteome Science 12:40, 1-13 (2014) (Year: 2014).*
Aitchison et al., RASSF1A promoter methylation is frequently detected in both pre-malignant and non-malignant microdissected prostatic epithelial tissues (2007) Prostate 67, 638-644.
Brooks et al. Prostate Cancer Screening 2010: Updated Recommendations From the American Cancer Society (2010) J.Natl.Med. Assoc. 102(5), 423-429.
Chandran et al., Differences in gene expression in prostate cancer, normal appearing prostate tissue adjacent to cancer and prostate tissue from cancer free organ donors (2005) BMC Cancer 5, 45.
Gann et al., Risk Factors for Prostate Cancer Detection After a Negative Biopsy: A Novel Multivariable Longitudinal Approach (2010) J. Clin. Oncology, vol. 28(10), 1714-1720.
Hanson et al., Gene Promoter Methylation in Prostate Tumor—Associated Stromal Cells (2006) J. Natl. Cancer Inst. 98, 255-261.
Henrique et al., Epigenetic Heterogeneity of High-Grade Prostatic Intraepithelial Neoplasia: Clues for Clonal Progression in Prostate Carcinogenesis (2006) Mol Cancer Res 4, 1-8.
Jemal et al., Cancer Statistics, 2009 (2009) CA Cancer J Clin 59, 225-249.
Nonn et al., Evidence for field cancerization of the prostate (2009) Prostate 69, 1470-1479.
Paradowska, et al., Aberrant epigenetic modifications in the CTCF binding domain of the IGF2/H19 gene in prostate cancer compared with benign prostate hyperplasia (2009) International Journal of Oncology 35, 87-96.
Schröder et al., Screening and Prostate-Cancer Mortality in a Randomized European Study (2009) The New England Journal of Medicine, vol. 360(13), pp. 1320-1328.
Schulz et al., Epigenetic mechanisms in the biology of prostate cancer (2009) Semin Cancer Biol 19, 172-180.
Thompson et al., Prevalence of Prostate Cancer among Men with a Prostate-Specific Antigen Level ≤4.0 ng per Milliliter (2004) N Engl J Med 350, 2239-2246.
Yu, et al. Gene Expression Alterations in Prostate Cancer Predicting Tumor Aggression and Preceding Development of Malignancy (2004) Journal of Clinical Oncology, vol. 22(14), pp. 1-10.
Gertych et al: "Machine learning approaches to analyze histological images of tissues from radical prostatectomies", Computerized Medical Imaging and Graphics, Pergamon Press, New York, NY, US, vol. 46, Aug. 20, 2015 (Aug. 20, 2015), pp. 197-208.
Chen et al: "Epithelium percentage estimation facilitates epithelial quantitative protein measurement in tissue specimens", Clinical Proteomics, Biomed Central Ltd, London, UK, vol. 10, No. 1, Dec. 1, 2013 (Dec. 1, 2013), p. 18.
Robert et al: "Percentage area density of epithelial and mesenchymal components in benign prostatic hyperplasia: comparison of results between single biopsy, multiple biopsies and multiple tissue specimens", British Journal of Urology, vol. 75, No. 3, Mar. 1, 1995 (Mar. 1, 1995), pp. 317-324.

(Continued)

*Primary Examiner* — Dennis Heyer
(74) *Attorney, Agent, or Firm* — Quarles & Brady LLP (57) ABSTRACT

A method of detecting the presence of a prostate cancer in a human subject comprising the steps of (a) obtaining a histologically normal prostate tissue sample from the patient and (b) quantifying the epithelial percentage of the tissue, wherein an epithelial percentage greater than 39% indicates the presence of prostate cancer or a prostate cancer field defect.

13 Claims, 4 Drawing Sheets
(2 of 4 Drawing Sheet(s) Filed in Color)

(56) References Cited

OTHER PUBLICATIONS

Nuzzo et al: "Prognostic value of stromal and epithelial periostin expression in human prostate cancer: correlation with clinical pathological features and the risk of biochemical relapse or death," BMC Cancer, Biomed Central, vol. 12, No. 1, Dec. 28, 2012, p. 625.
Montironi et al: "Subtle morphological and molecular changes in normal-looking epithelium in prostates with prostatic intraepithelial neoplasia or cancer," European Urology, vol. 35, No. 5-6, May 1999, p. 468-473.
International Search Report and Written Opinion for PCT/US2017/061544, dated Feb. 22, 2018, 16 pages.

* cited by examiner

EPITHELIAL QUANTITATION OF HISTOLOGICALLY NORMAL PROSTATE TISSUE PREDICTS THE PRESENCE OF CANCER IN TISSUE BIOPSIES

CROSS-REFERENCE TO RELATED APPLICATION

This application claims the benefit of U.S. Provisional Patent Application No. 62/421,554 filed Nov. 14, 2016.

STATEMENT REGARDING FEDERALLY SPONSORED RESEARCH OR DEVELOPMENT

This invention was made with government support under CA193481 awarded by the National Institutes of Health. The government has certain rights in the invention.

BACKGROUND

It is estimated that 198,280 men were diagnosed with prostate cancer and 27,360 men died from prostate cancer (PCa) in 2009 in the USA (Jemal et al., (2009) *CA Cancer J Clin* 59, 225-249). The predominant tools for early detection of prostate cancer are prostate specific antigen (PSA) testing and digital rectal exam (DRE). However, 65% to 70% of men with total PSA ranging between 4.0-10.0 ng/ml have a negative prostate biopsy result. In addition, 15% of PCa patients have PSA levels <4.0 ng/ml, indicating a weak predictive ability (Thompson et al., (2004) *N Engl J Med* 350, 2239-2246). PSA-based screening also detects non-significant cancers leading to an estimated 50% of overdiagnosis (Fritz et al., (2009) *The New England Journal of Medicine* 360). A urine-based test examining an RNA molecule termed PCA-3 is currently undergoing FDA trials. Prostate biopsy is used to confirm disease. However, because of sampling errors repeated sets of samples are commonly required to make a diagnosis (Gann et al., (2010) *JCO* 28, 7). Typical biopsy schemes include 10-12 or more tissue cores removed under local anesthetic. Re-biopsy is often required two to three times in order to rule out cancer because of sampling errors. Cancers can also be missed because of sampling problems.

There is a clear need for methods that allow easier and more accurate diagnosis and prognosis of prostate cancer.

SUMMARY OF THE INVENTION

In a first aspect, the present invention is a method of treating prostate cancer in a human subject comprising the steps of, obtaining histologically normal prostate tissue from the subject, quantifying epithelial percentage in the tissue; and treating the human subject for prostate cancer when the epithelial percentage is greater than 39%. In one embodiment, the epithelial percentage is greater than 40%.

In a second aspect, the present invention is a method of treating prostate cancer in a human subject comprising the steps of obtaining histologically normal prostate tissue from the subject, staining the tissue, imaging the tissue, quantifying epithelial percentage in the tissue, and treating the human subject for prostate cancer when the epithelial percentage is greater than 39%. In one embodiment, the epithelial percentage is greater than 40%.

In certain embodiments of the invention, the tissue is stained with a stain specific for epithelial cells. In some embodiment, the stain is hematoxylin and eosin stain. In some embodiments, the stain is a high molecular weight cytokeratin stain. In some embodiments, the epithelial cells are quantified using a marker specific to epithelial cells.

In certain embodiments, the tissue is imaged using an automated imaging system. In some embodiments, the automated imaging system is selected from the group consisting of VECTRA™, Aperio eSlide Manager, TissueFAXS 220, TissueFAXS CONFOCAL PLUS 200. In some embodiments, the epithelial percentage is quantified using image analysis software. In one embodiment, the image analysis software is inForm2.1.1.

In a third aspect, the present invention is a method of detecting and quantifying epithelial cells in a human subject suspected of having prostate cancer comprising the steps of, obtaining histologically normal prostate tissue from the subject, and quantifying epithelial percentage in the tissue. In certain embodiments, the method may also include the step of evaluating the human subject for prostate cancer when the epithelial percentage is greater than 39%. In one embodiment, the epithelial percentage is greater than 40%.

In a fourth aspect, the present invention is a method of treating prostate cancer in a human subject comprising the steps of, obtaining histologically normal prostate tissue from the subject, quantifying in the tissue a marker specific to epithelial cells, wherein a significant increase in the epithelial specific marker indicates the presence of prostate cancer or a prostate cancer field defect, wherein the change is relative to tissue from a second human subject who does not have prostate cancer; and treating the human subject for prostate cancer based on the results of steps (a) and (b).

BRIEF DESCRIPTION OF DRAWINGS

This patent application file contains at least one drawing executed in color. Copies of this patent or patent application publication with color drawings will be provided by the Office upon request and payment of the necessary fee.

The invention will be better understood and features, aspects and advantages other than those set forth above will become apparent when consideration is given to the following detailed description thereof. Such detailed description makes reference to the following drawings, wherein:

FIGS. 1A-1B show H&E slides from histologically normal prostate tissue before and after segmentation. An H&E slide was scanned using a 4× magnification, the biopsy tissue strips were aligned, stored, and accessed as an entire image, and the regions of interest were segmented into epithelial and stromal cells using the image analysis software-inForm2.1.1. Stained tissues are colored as follows—epithelium (red), stroma (green), and blank (purple). (A) A non-tumor associated (NTA) histologically normal prostate tissue sample generated 19.6% epithelial percentage of total cells after segmentation of the image into epithelium, stroma, and background regions. (B) A tumor associated (TA, e.g. from a patient with cancer elsewhere in the prostate) histologically normal prostate tissue sample yields 46.7% epithelial percentage in this example.

FIG. 3 shows a logistic regression analysis for the patient samples in FIG. 2. Receiver Operating Curves (ROC) were generated to assess the predictive accuracy of uniplex-E % regression model for discriminating TA and NTA biopsy negative cores. AUC=0.692, p<0.05. Note: PSA testing the standard approach in this setting only generates an ROC of 0.56.

FIG. 4 shows additional epithelial percentage data from a different patient dataset. Images of H & E stained biopsy slides prostate were obtained using automated quantitative imaging system VECTRA™ system, and then analyzed using image software-inForm2.1.1. The area of epithelia and stroma was measured and the epithelial % is calculated as epithelium area/(epithelium area+stroma area). Analysis of a validation patient dataset TA (n=31) versus NTA (n=28) was performed. Choosing peripheral zone specific biopsies from the mid prostate where prostate cancer arises demonstrated improved discrimination between TA (46%) vs NTA (39%), (p=0.02). This data demonstrates that apparent normal prostate tissue from men that have cancer has an increased epithelial component compared to men without cancer.

DESCRIPTION OF THE PRESENT INVENTION

In General

Like other human cancers, prostate cancer development and progression is driven by the interplay of genetic and epigenetic changes (Schulz et al., (2009) *Semin Cancer Biol* 19, 172-180). Genetic and epigenetic alterations do not appear to be limited to the cancerous cells, as recent data indicates tissue adjacent or distant to the tumor is also abnormal (Nonn et al., (2009) *Prostate* 69, 1470-1479). This field defect (also termed field effect) has been identified in colon and head and neck cancer, as well as prostate based on alterations in gene expression (YP, Y. (2004) *Journal of Clinical Oncology* 22; Chandran et al., (2005) *BMC Cancer* 5, 45) and genomic loss of imprinting (Agnieszka et al., (2009) *International Journal Of Oncology* 35, 87-96). Aberrant methylation patterns in the GSTP1, RARb2, APC and RASSF1A promoters have been detected in normal epithelial or stromal tissue adjacent to cancer (Aitchison et al., (2007) *Prostate* 67, 638-644; Hanson et al., (2006) *J. Natl. Cancer Inst.* 98, 255-261; Henrique et al., (2006) *Mol Cancer Res* 4, 1-8). These genes are altered in the tumor and represent a single gene approach to analyzing the field effect. These gene alterations may increase the proliferation or decrease cell death in epithelial cells, the cell of origin for prostate cancer. This may potentially underlie alterations in epithelial number in men whose prostates contain cancer elsewhere.

By use of the present invention, one can reassure men who have a negative biopsy that no cancer is present by quantifying epithelial percentage without additional future biopsies and avoid the complications directly associated with increasing the biopsy number and frequency. If a high epithelial percentage is detected, more detailed imaging with an MRI and endorectal probe and a more aggressive detection strategy requiring anesthesia and 30-50 biopsies will typically be undertaken to detect and/or characterize the disease. This approach is associated with additional risks associated with anesthesia, infection, bleeding and others, and is not performed routinely. In addition, it is likely these patients would be monitored much more closely. Applicants have demonstrated additional methods for the identification of prostate cancer field defects. See, e.g., U.S. Published Patent Application Nos. 2012/0135877 and 2014/0296355. Each published patent application is incorporated herein by reference as if set forth in its entirety.

In developing the present invention, the inventors have analyzed histologically normal tissues from men with and without prostate cancer utilizing automated quantitative image analysis to determine epithelial percentage. The inventors associated an increased epithelial percentage with the presence of prostate cancer. Analysis of epithelial percentage in tissue samples from patients will enhance the detection of prostate cancer.

By "histologically normal", we mean prostate tissue that has no evidence of disease in the specimen itself, based on standard morphologic and histochemical criteria used by pathology. By "normal" or "non-tumor associated (NTA)", we mean a prostate specimen that not only does not contain cancer itself, as defined by a pathologist, but also does not contain cancer elsewhere in the prostate. By "tumor associated (TA)", we mean a prostate specimen which does not show evidence of cancer, but is taken from a prostate with evidence of cancer in another location. One would appreciate that both "non-tumor associated" and "tumor associated" prostate specimens in this application are "histologically normal" prostate specimens. In one embodiment, histologically normal tissues are substantially free of prostatic intraepithelial neoplasia (PIN) or other pathological abnormalities. In one embodiment, histologically normal tissue samples are evaluated to exclude any cancer.

The term "epithelial percentage," as used herein refers to the percentage of a given tissue sample which comprises epithelial cells as a percentage of total epithelial and stromal cells. Epithelial percentage is quantified as the area defined as epithelial divided by the total area of both epithelial and stromal. In one embodiment, automated imaging of stained tissue is used to identify a given area as epithelial or stromal and the epithelial percentage is calculated as the epithelial pixel area of the image divided by the total of the epithelial pixel area and the stromal pixel area.

The term "epithelium" refers to layers of cells that line hollow organs and glands. It is also those cells that make up the outer surface of the body. Epithelial cells help to protect or enclose organs. All glands are made up of epithelial cells as in this situation in the prostate. Functions of epithelial cells include secretion, selective absorption, protection, transcellular transport, and sensing. The term "stromal" refers to cells that are connective tissue cells of any organ, for example in the uterine mucosa (endometrium), prostate, bone marrow, and the ovary. Stromal cells support the function of the parenchymal cells of that organ. Epithelial cells are the origin of prostate cancer. Fibroblasts and pericytes are among the most common types of stromal cells. The interaction between stromal cells and tumor cells is known to play a major role in cancer growth and progression.

Embodiments of the Present Invention

In one embodiment, one can diagnose and/or treat prostate cancer in a human subject by quantifying the epithelial percentage in histologically normal tissue biopsy specimens taken from men who may have prostate cancer. Based on the results of the detection methods described herein, the subject may be diagnosed with prostate cancer and/or treated for prostate cancer via conventional therapies.

It is an advantage of the present invention that fewer biopsies are needed for the detection of prostate cancer. In a preferred embodiment, the presence of a epithelial percentage can be detected based on only 1-2 core biopsy specimens taken from anywhere in the prostate. In addition, in individuals who have had a negative biopsy but whose PSAs continue to rise, analysis of the previously obtained specimens for epithelial percentage in histologically normal tissue will direct whether additional evaluation needs to be performed.

In one embodiment, if the epithelial percentage is higher than 39%, a more intensive biopsy set requiring anesthesia would be performed. If not, the patient can be reassured. In one embodiment, an epithelial percentage higher than about 39% (e.g. at least about 38%, 39%, 40%, 41%, 42%, 43%, 44%, 45%, 50%, 55%, 60% or 70%) is indicative of associated prostate cancer. In some embodiments, the epithelial percentage is between about 39% and 80% (e.g. between about 39% and 80%, 39% and 75%, 40% and 70%, 45% and 55%).

To examine the epithelial percentage in histologically normal tissues, one would typically wish to obtain histologically normal tissue samples from a patient and prepare said tissue samples for microscopic analysis. Samples may be obtained from a prostate biopsy. In one typical embodiment, prostate tissue samples are obtained via standard transrectal ultrasound and biopsy protocols using an 18 gauge needle (Brooks et al. (2010) J. Natl. Med. Assoc. 102(5), 423-429). In another embodiment, prostate tissues are obtained from paraffin blocks of prostate biopsy samples that have already been obtained and examined.

Preparation of the tissue samples will involve staining the tissue samples with a stain specific to epithelial cells. Any stain known in the art specific to epithelial cells may be used. Stains may include, but are not limited to, hematoxylin and eosin (H&E) stain; immunofluorescence staining for epithelial markers including cytokeratin, E-cadherin, keratin 8 or EpCam; or immunofluorescence staining combined with stroma staining using Sirius red with picric acid. In one embodiment, tissue samples are stained using H&E stain. In one embodiment, tissue samples are formalin fixed and paraffin embedded prior to staining.

In some embodiments, the stain is a high molecular weight cytokeratin. Cytokeratins are keratin proteins found in the intracytoplasmic cytoskeleton of epithelial tissue. They are an important component of intermediate filaments, expression of these cytokeratins within epithelial cells is largely specific to particular organs or tissues. After deparaffinizing and rehydrating the tissue section slide, boil the slide in sodium citrate for antigen retrieval. Permeabilize the section, block the non-specific binding with animal serum, and then stain the slide with anti-human pan-cytokeratin overnight at 4° C. in humidified chamber, wash off the slide and then add secondary antibody at room temperature for 1-2 hours. Finally apply DAPI to the slide for 5 minutes to reflect the total cell staining. Slide image is obtained using automated quantitative imaging system VECTRA™ system, and then analyzed using image software-inForm2.1.1. Epithelium % is calculated as the positive staining of cytokeratin.

In another aspect of the invention, preparation of the tissue samples will involve quantification of any maker known to be specific to epithelial cells. Markers specific to epithelial cells that may be quantified in the methods of the present invention include, but are not limited to, Epcam, E-cadherin, and Cytokeratin. Without wishing to be bound by any particular theory, it is understood that an increase in epithelial percentage in an indicator of a prostate cancer field defect in a patient, and therefore, any marker specific to an epithelial cell will also necessarily be increased in the prostate tissue being analyzed. Quantification of epithelial cells may be carried out by quantifying the levels of epithelial specific markers by standard laboratory approaches used for quantifying RNA or protein levels including PCR and/or western blot. A significant increase in the level of these epithelial markers, as compared to the level of the same epithelial marker in normal tissue from men with no history of prostate cancer, would indicate the presence of prostate cancer or a prostate cancer field defect. A significant increase is any statistically meaningful change in quantification relative to quantification in normal tissue from men with no history of prostate cancer. For example, significant change may be characterized by a p value less than 0.05.

Following staining, tissue samples may be imaged by any means known in the art. Tissue samples may be imaged manually or automatically. In one embodiment, tissue samples are imaged automatically. In one embodiment, tissue samples are imaged using an automated quantitative imagine system. Automated quantitative image systems may include, but are not limited to VECTRA™ (Perkin Elmer, Waltham, Mass.), Aperio eSlide Manager (Leica Biosystems, Buffalo Grove, Ill.), TissueFAXS 220, TissueFAXS CONFOCAL PLUS 200 (TissueGnostics, Vienna, Austria), and the like.

Estimates of epithelium and stromal content in histologically normal prostate tissue samples or images of the prostate tissue samples may be done by any means known in the art. In one embodiment, the epithelial and stromal regions are estimated by semiquantitative visual review by one of skill in the art. In one embodiment, the epithelial and stroma regions are estimated by automated image analysis.

The term "automated image analysis," as used herein refers to an automated method for the analysis and quantification of epithelium and stromal content in a tissue sample. The steps of automated image analysis using image analysis software may typically include (1) manual definition of epithelium, stromal, and background regions of the images, (2) training of the software to recognize epithelium, stromal, and background regions of the images as manually defined, (3) automated segmentation of images into epithelium, stromal and background regions, (4) quantification of the area of each of the epithelium, stromal, and background regions of the images using an algorithm specific to the software. Automated image analysis software may include, but are not limited to inForm2.1.1, StrataQuest 5.0 software, Aperio GENIE Image Analysis, and the like. In one embodiment, the automated image analysis software is inForm2.1.1. In one embodiment, the automated image analysis software is integrated within the automated quantitative image system.

Methods described herein are used to determine the epithelial percentage of a sample of histologically normal prostate tissue. It is understood in the art that the particular imaging systems and analysis software used may generate different relative epithelial percentages for a single tissue sample. The percentages as quoted herein reflect the percentage as calculated using a VECTRA™ (Perkin Elmer, Waltham, Mass.) automated quantitative imagining system and inForm2.1.1 image analysis software. In one embodiment, an epithelial percentage greater than 39%, as measured by the method described in the previous sentence, is indicative of prostate cancer. In one embodiment an epithelial percentage greater than 40% is indicative of prostate cancer. In another embodiment an epithelial percentage greater than 41% is indicative of prostate cancer.

The Examples focus on a preferred method, but one of skill in the art would understand that other methods would be suitable.

EXAMPLES

Prostate cancer is the most commonly diagnosed disease in men and the typical approach to diagnosing the presence of prostate cancer in an individual with an elevated PSA is a prostate biopsy, typically using 10-12 cores. However, only 25-30% of these biopsies are found to be positive, leaving approximately 15% of prostate cancers undiagnosed. Prostate biopsy is associated with infection, pain, and bleeding. A common scenario is the need for repeated biopsies in patients with a persistently elevated PSA and negative histological findings. The availability of these histologically normal prostate biopsy specimens is a potential resource that could help, with the proposed methods, to confirm the presence or absence of prostate cancer.

Computer-based analysis of digital pathology images is a recent development that has allowed the extraction of image-based features from histologic tissue. Previous efforts have focused on cancer tissue and immediate adjacent normal tissue not comparing this normal tissue to men without cancer in their prostates. Automated imaging and analysis is rapid and quantitative and does not require special stains or additional samples from patients. We sought to identify morphometric features of histologically normal prostate tissue that may vary between the patients with and without prostate cancer, which could be used as quantitative for epithelial percentage.

Materials and Methods

Figures 1A, 1B:
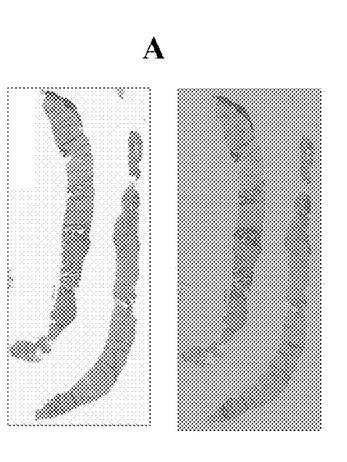
Figure 2:
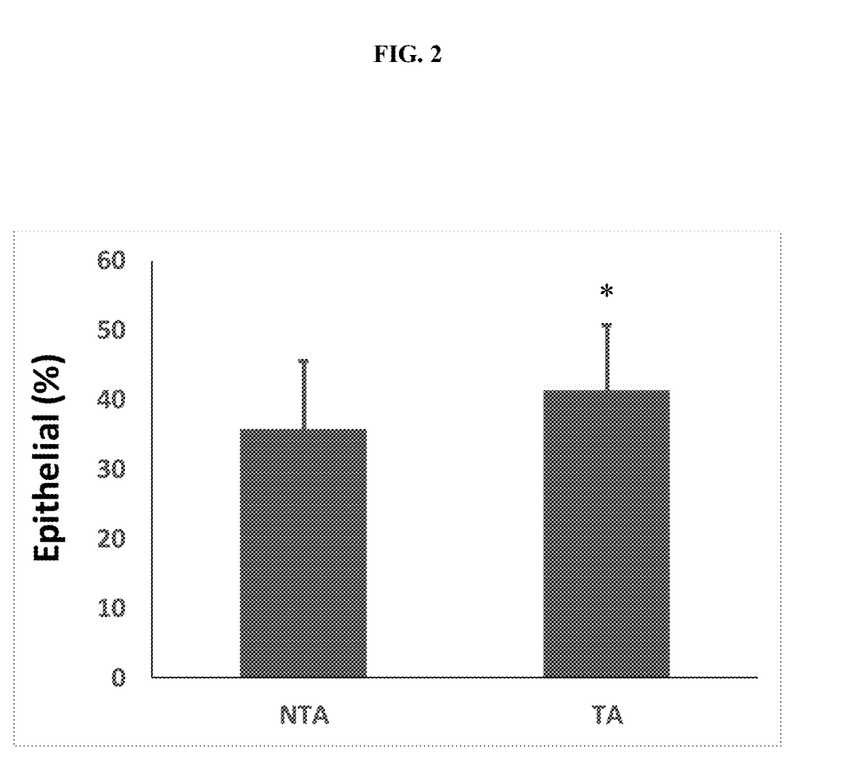
FIG. 2 shows the epithelial percentage in NTA and TA across a series of patient samples. The data shows epithelial percentage for the histologically normal prostate biopsies from the patients with prostate cancer (TA, n=27) and without prostate cancer (NTA, n=20). The data is shown as Mean±SD. *p<0.01, TTEST.
Figure 3:
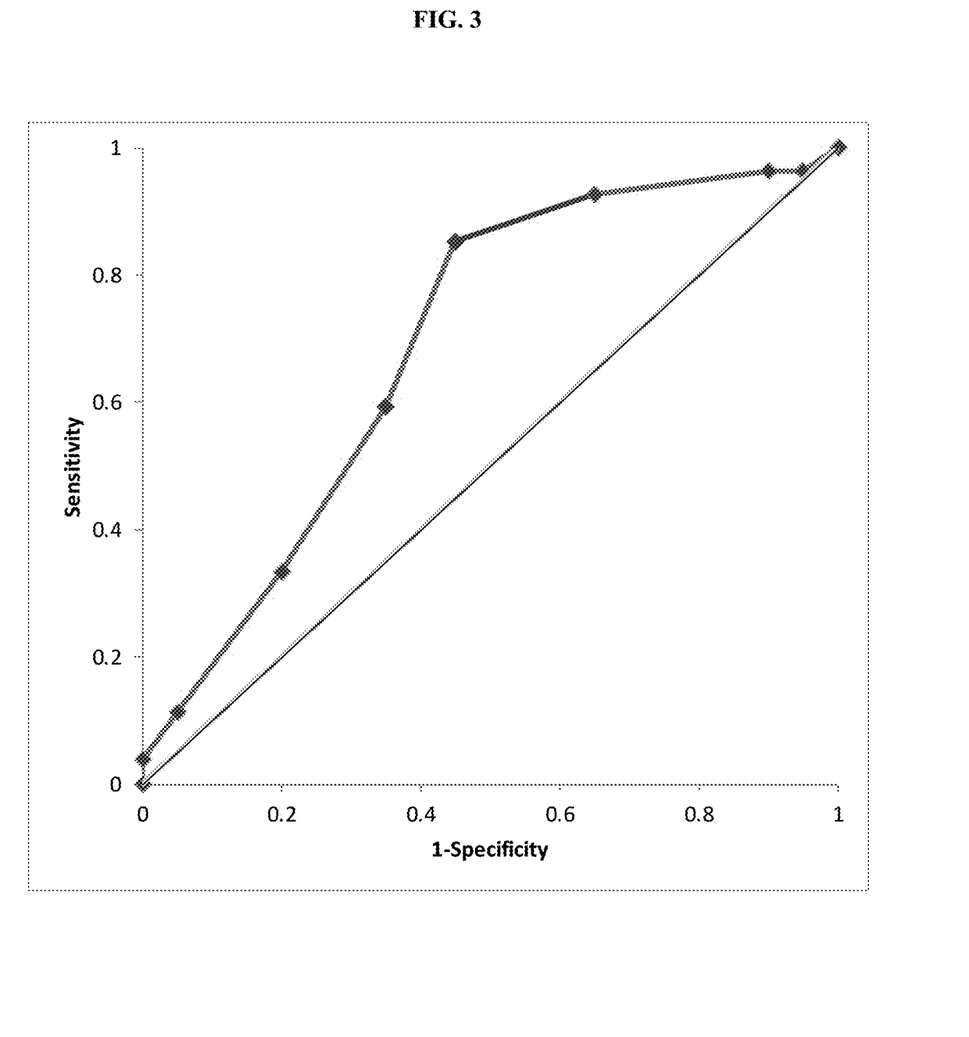
Figure 4:
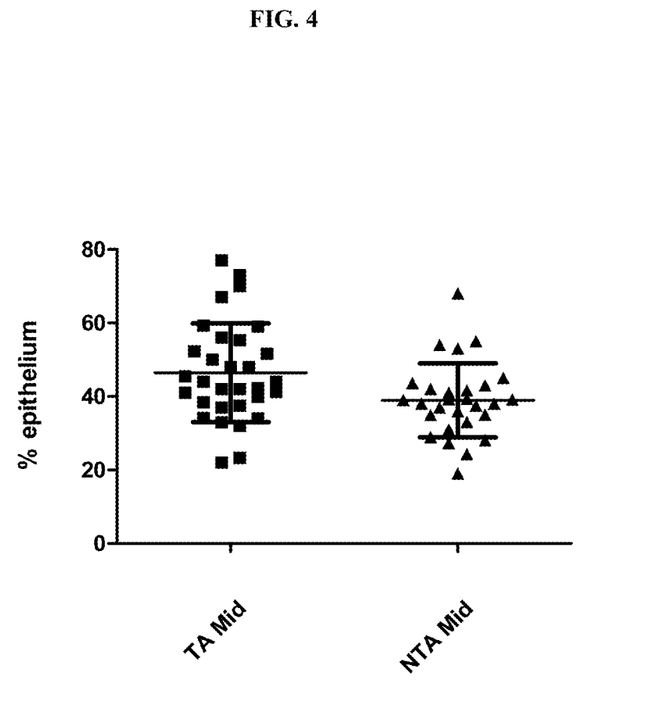

We requested H&E staining slides of formalin fixed—paraffin embedded (FFPE) prostate biopsy tissues from the University of Wisconsin-Madison. Patients were considered eligible if they had 10-12 cores taken during prostatic needle-core biopsy, no earlier than 2011. Patients must also have been between the ages of 52-70 at the time of biopsy, had a prostate mass of <60 g upon ultrasound, and had a PSA level between 3-10 ng/ml. It is important to note that only histologically normal appearing slides were analyzed in this trial. Forty-seven (47) separate patient cases were examined, with at least 2 sections from each patient analyzed. Twenty-seven (27) were from the patients that have associated cancer (TA) with cancer found on 1-6 cores upon biopsy; and twenty (20) were from the patients who had no evidence of cancer (NTA) with two or more negative prostate biopsies within a 24-month period. All cases containing prostatic intraepithelial neoplasia (PIN) or other pathologic abnormalities were not included and all slides were evaluated by a prostate cancer pathologist to exclude any cancer. A validation study (FIG. 4) also demonstrated this change.

Tissue processing and slide preparation: A color-based segmentation method was developed in-house for estimation of epithelium content using H&E (hematoxylin and eosin) histology slides from biopsies. All sections are 20 μm in width and 5 μm in thickness, and were H&E stained. All H&E histology slides were scanned with a 4× objective using the automated quantitative imaging system VECTRA™ (Perkin Elmer, Waltham, Mass.) in the UW-Madison Translational Pathology Laboratory. The line scan camera captures tiles stripes across the entire slide, the stripes are aligned, stored, and accessed as an entire image of each slide. Slides with poor resolution or significant folded tissue were excluded from analysis.

Definition of the regions of epithelium and stromal tissue: The images of the sections were then analyzed using image analysis software-inForm2.1.1. The most important and difficult step in automatic image analysis is the image segmentation, which provides critical information for further image interpretation. First ten images were randomly selected for training. Under supervision of an experienced pathologist, regions of epithelium, stromal and blank were drawn manually using the zooming and mark-up tools included in the software. The epithelial region was drawn around the epithelial cells located on the border to the stromal to avoid any inclusion of area which contains exclusively stromal. Artifacts such as folded or broken tissue areas or areas showing strong background staining due to tissue debris were excluded from the analysis. For a training set of images, some of the epithelial, stromal, and background areas are manually framed in different colors. Following the training on areas of the images, the software specific annotation algorithm then segments the reminder of the image into epithelial, stromal, and background areas and quantifies the area of each. The epithelium contents of the training slides were also estimated by the pathologist. After the results of the pathologists semi-quantitative visual review and the software specific annotation algorithm showed excellent concordance, the algorithm was applied to the rest of the slides. Segmentation of each slide by the software was reviewed carefully before analysis. Epithelial and stromal pixel areas were generated automatically by the software after segmentation.

Statistical Analysis: Epithelial percentage was calculated as (epithelial pixel area)/(epithelial pixel area+stromal pixel area), and epithelium/stromal ratio was calculated as (epithelial pixel area)/(stromal pixel area). Since at least 2 sections from each patient were used, mean values were used to determine significant differences between NTA and TA cohorts. Mean values for epithelial percentage and epithelial/stromal ratio were calculated by averaging the epithelial percentage and epithelial/stromal ratio of all sections for that cohort. TTEST was performed to analyze the significant differences between NTA and TA cohorts. A logistic regression model was used to test the correspondence of the epithelial percentage and epithelial/stromal ratio to a prediction of the presence of cancer. Area under the curve (AUC) values, as well as p-values, were also calculated. All statistical analyses were performed by a certified statistician from the University of Wisconsin-Madison using SAS v.9.4 (SAS Institute, Cary, N.C., USA).

Results

Epithelial percentage analysis demonstrated that the epithelium percentage for TA tissues (41.4%) was significantly higher than NTA tissues (35.7%) ($p<0.01$). The epithelial/stromal ratio was also significantly different between TA and NTA tissues ($p<0.01$; 0.753 and 0.593, respectively). An area under the curve (AUC) using this measurement demonstrated 0.692 with a p-value of 0.02. An AUC of 0.69 means 69 out of 100 chances you predict the presence of prostate cancer correctly. In medical biomarker studies it is a common method to measure sensitivity and specificity using a Receiver Operating Characteristic (ROC) curve. ROC curves plot the sensitivity of a biomarker on the y axis, against the false discovery rate (1—specificity) on the x axis. ROC curves provide a simple visual method for one to determine the boundary limit (or the separation threshold) of a biomarker or a combination of biomarkers for the optimal combination of sensitivity and specificity. The AUC (area under the curve) of the ROC curve reflects the overall accuracy and the separation performance of the biomarker (or biomarkers) and can be readily used to compare different biomarker combinations or models. This segmentation analysis revealed that the epithelium percentage within normal tissue predicts the presence of associated cancer and could be used as a device to avoid biopsies.

We have found that developing an estimation of the epithelial percentage in prostate biopsy specimens from H&E stained sections is an independent predictor for the presence of prostate cancer in the absence of tumor associated biopsy tissue, and can be used as a device to avoid repeat biopsies. To date computer analysis of normal tissue has focused on tissue adjacent to cancer and its role in predicting cancer outcomes. As demonstrated herein, analysis of epithelium in negative biopsies indicated that a computer based imaging approach quantifying the amount of epithelium could demonstrate a difference between normal tissues from cancer and noncancer patients.

We claim:

1. A method of treating prostate cancer in a human subject comprising the steps of:
   (a) obtaining histologically normal prostate tissue from the subject;
   (b) quantifying epithelial percentage greater than 39% in the histologically normal prostate tissue; and
   (c) treating the human subject for prostate cancer.

2. The method of claim 1, additionally comprising the steps of
   (i) staining the tissue; and
   (ii) imaging the tissue prior to the step of quantifying epithelial percentage in the stained, imaged tissue.

3. The method of claim 2, wherein the tissue is stained with a stain specific for epithelial cells.

4. The method of claim 3, wherein the stain is hematoxylin and eosin stain.

5. The method of claim 3, wherein the stain is a high molecular weight cytokeratin stain.

6. The method of claim 2, wherein the tissue is imaged using an automated imaging system.

7. The method of claim 6, wherein the automated imaging system is selected from the group consisting of VECTRA™, Aperio eSlide Manager, TissueFAXS 220, TissueFAXS CONFOCAL PLUS 200.

8. The method of claim 2, wherein the epithelial percentage is quantified using image analysis software.

9. The method of claim 8, wherein the image analysis software is inform 2.1.1.

10. The method of claim 1, wherein the epithelial percentage is greater than 40%.

11. The method of claim 2, wherein the epithelial percentage is greater than 40%.

12. The method of claim 1, wherein the epithelial percentage is between 39% and 80%.

13. The method of claim 2, wherein the epithelial percentage is between 39% and 80%.

* * * * *

UNITED STATES PATENT AND TRADEMARK OFFICE
CERTIFICATE OF CORRECTION

PATENT NO. : 10,598,664 B2
APPLICATION NO. : 15/812015
DATED : March 24, 2020
INVENTOR(S) : David Frazier Jarrard et al.

It is certified that error appears in the above-identified patent and that said Letters Patent is hereby corrected as shown below:

In the Claims

Column 10, Claim 9, Line 12, "is inform 2.1.1" should be --is inForm2.1.1--.

Signed and Sealed this
Nineteenth Day of May, 2020

Andrei Iancu
*Director of the United States Patent and Trademark Office*